United States Patent [19]

Kato et al.

[11] Patent Number: 4,954,238

[45] Date of Patent: Sep. 4, 1990

[54] MOISTURE-SENSING HYGROMETER ELEMENT

[76] Inventors: Hiroshi Kato, 123, Minamigata, Yoshinaga-cho, Wake-gun; Eiichi Torikai, 9-20, 3-chome, Higashikyuhoji, Yao-Shi, Osaka-Fu, both of Japan

[21] Appl. No.: 314,642

[22] Filed: Feb. 23, 1989

[30] Foreign Application Priority Data

Feb. 23, 1988 [JP] Japan ................................ 63-38528

[51] Int. Cl.$^5$ ............................................. G01N 27/26
[52] U.S. Cl. .................................... 204/430; 73/336.5; 204/153.22; 338/35
[58] Field of Search ............. 204/1 W, 430; 73/336.5, 73/336, 335; 338/35

[56] References Cited

U.S. PATENT DOCUMENTS

| | | | |
|---|---|---|---|
| 3,001,918 | 9/1961 | Czuha | 204/430 |
| 3,240,693 | 3/1966 | Gardner | 204/430 |
| 3,295,088 | 12/1966 | Smith | 338/35 |
| 3,458,845 | 7/1969 | Thoma | 73/336.5 |
| 3,954,590 | 5/1976 | Czuha | 204/430 |
| 3,978,006 | 8/1976 | Topp et al. | 204/429 |
| 4,083,765 | 4/1978 | Lawson | 204/430 |
| 4,502,939 | 3/1985 | Holfelder et al. | 204/426 |

FOREIGN PATENT DOCUMENTS

| | | | |
|---|---|---|---|
| 3058249 | 3/1988 | Japan | 204/430 |
| 545913 | 2/1977 | U.S.S.R. | 204/430 |
| 642643 | 1/1979 | U.S.S.R. | 204/430 |

*Primary Examiner*—T. Tung
*Attorney, Agent, or Firm*—Mortenson & Uebler

[57] ABSTRACT

A moisture-sensing hygrometric element is provided comprising an electrolytic moisture-sensing mechanism integrally formed on the surface of a porous substrate, the porous substrate being resistant to oxidation and reduction and resistant to acids, wherein the moisture-sensing mechanism comprises a pair of platinum group metal electrodes constituting an anode and a cathode and having a fluororesin-type cation exchange resin membrane layer thereover. The porous substrate may be porous ceramic or a porous fluororesin such as expanded polytetrafluoroethylene. The hygrometric element may have an additional covering layer thereover of porous, expanded polytetrafluoroethylene. Also provided is a method for manufacturing the moisture-sensing hygrometric element.

3 Claims, 2 Drawing Sheets

MOISTURE-SENSING HYGROMETER ELEMENT

BACKGROUND OF THE INVENTION

The present invention relates to a moisture-sensing hygrometric element which measures the humidity of the atmosphere by performing a humidity-current or humidity-voltage conversion resulting from the electrolysis of water.

In the past, ceramics and polymers have generally been used as moisture-sensing element materials for measuring humidity. Ordinarily, such elements have used a detection means based on a resistance system or an electrostatic capacity system. However, elements of both of these types have been somewhat unsatisfactory in terms of ease of handling, high-precision measurement across a broad humidity range and useful life. Few of these elements can be used in a corrosive atmosphere.

A method which utilizes the electrolysis of water to measure the humidity of a gas has been disclosed in U.S. Pat. No. 4,083,765. Specifically, a sensor is proposed which uses a tube made of a fluororesin-type cation exchange resin containing sulfonic acid groups as ion exchange groups, and in which platinum is caused to contact the internal and external surfaces of the tube in coil form as electrodes. Since the materials used are intrinsically superior in terms of corrosion resistance, this sensor can be used in a corrosive atmosphere. A linear correlation between humidity and current across a broad humidity range is provided.

The use of an assembly in which electrodes are bonded to both surfaces of a fluororesin ion exchange resin membrane as a moisture-sensing element has been proposed in Japanese Laid-Open Patent Application (Kokai) No. 60-36947.

The formation of an electrode pattern on the surface of an ion exchange resin membrane using a resist ink in order to increase the exposed surface area ratio of the ion exchange resin membrane has been proposed in Japanese Laid-Open Patent Application (Kokai) No. 61-264247.

In the case of the sensor disclosed in U.S. Pat. No. 4,083,765, a certain minimum film thickness is required in order to provide the fluororesin-type cation exchange resin membrane tube, which constitutes a solid polymer electrolyte, with adequate mechanical strength. As a result, the capacity of the tube for containing water is very large, so that the response to humidity changes is slow in a static atmosphere. Furthermore, it is also structurally difficult to maintain a uniform contact between the tube and the electrode wire coils in long-term use. Since the output current changes with a change in the contact resistance, the reliability of the sensor is poor. In addition, in cases where the contact is poor so that the contact resistance is large, the current value is large when a high humidity is measured, so that heat is generated in the contact area, causing the tube to deteriorate.

In the case of the aforementioned moisture-sensing element disclosed in Japanese Laid-Open Patent Application (Kokai) No. 60-36947, the abovementioned problem of the contact resistance is solved. However, since virtually the entire surface of the membrane is covered by the electrodes, the exposed portion of the ion exchange membrane, which acts as the moisture-sensing element, is small so that the response to fluctuations in humidity is relatively poor.

Because oxygen and hydrogen are generated as electrolysis products at the electrodes, the equilibrium of the surrounding water vapor is disturbed, and the output tends to be unstable.

In the case of the sensor disclosed in Japanese Laid-Open Patent Application (Kokai) No. 61-264247, these problems are ameliorated by using a resist ink. In this case, however, the assembly must be formed by a complicated chemical plating process which includes the formation and removal of a resist ink pattern. As a result, it is difficult to obtain reproducible moisture-sensing characteristics, and it is also difficult to improve the yield and reduce manufacturing costs.

SUMMARY OF THE INVENTION

A moisture-sensing hygrometric element is provided comprising an electrolytic moisture-sensing mechanism integrally formed on the surface of a porous substrate, the porous substrate being resistant to oxidation and reduction and resistant to acids, wherein the moisture-sensing mechanism comprises a pair of platinum group metal electrodes constituting an anode and a cathode and having a fluororesin-type cation exchange resin membrane layer thereover. The cation exchange resin membrane may be porous. The porous substrate may be porous ceramic or a porous fluororesin such as expanded polytetrafluoroethylene. The hygrometric element may have an additional covering layer thereover of porous, expanded polytetrafluoroethylene. Also provided is a method for manufacturing a moisture-sensing hygrometric element comprising (a) installing an electrolytic moisture-sensing mechanism comprising an anode and cathode of platinum group metals on the surface of a porous substrate, the substrate being resistant to oxidation and reduction and resistant to acids, (b) coating the mechanism with a solution of a fluororesin-type cation exchange resin, and (c) heating and drying the solution, thereby forming a fluororesin-type cation exchange membrane over the electrolytic moisture-sensing mechanism.

Figure 1:
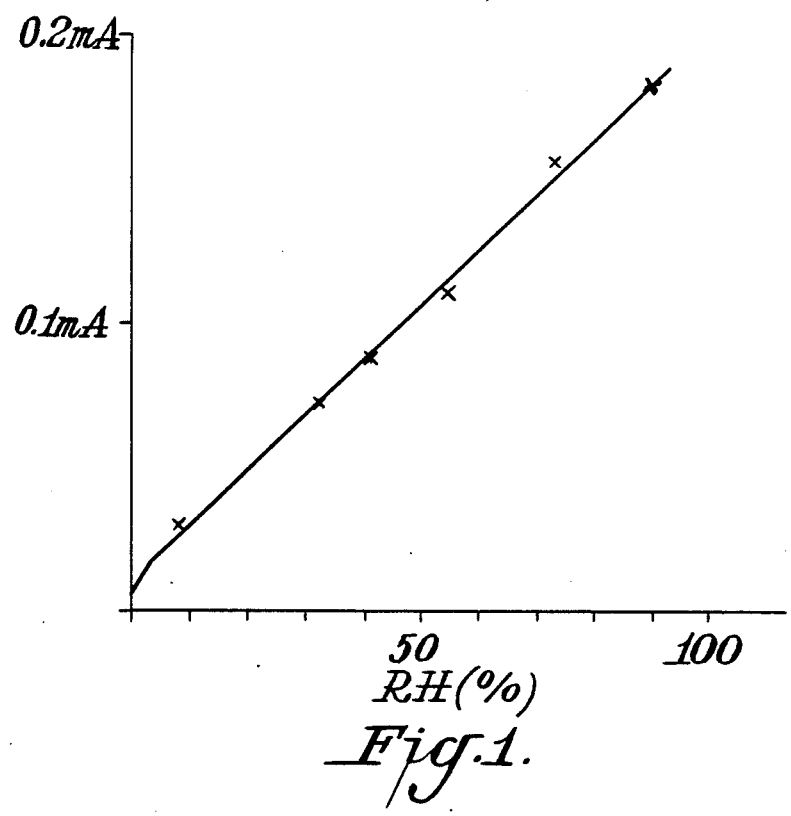
FIG. 1 is a graph of current density versus humidity measured using a moisture-sensing element according to the invention.

DETAILED DESCRIPTION OF THE INVENTION AND PREFERRED EMBODIMENTS WITH REFERENCE TO THE DRAWINGS

A moisture-sensing hygrometric element is provided comprising an electrolytic moisture-sensing mechanism integrally formed on the surface of a porous substrate, the porous substrate being resistant to oxidation and reduction and resistant to acids, wherein the moisture-sensing mechanism comprises a pair of platinum group metal electrodes constituting an anode and a cathode and having a fluororesin-type cation exchange resin membrane layer thereover. The porous substrate may be porous ceramic or a porous fluororesin such as expanded polytetrafluoroethylene. The hygrometric element may have an additional covering layer thereover of porous, expanded polytetrafluoroethylene. Also provided is a method for manufacturing the moisture-sensing hygrometric element.

More specifically, the present invention concerns a moisture-sensing element which is based on the principle of water electrolysis. An object of the present invention is to provide a moisture-sensing element which substantially solves the problems associated with conventional elements, which element has a rapid response, which allows high-precision humidity measurements to be made across a broad humidity range, and which has a long useful life and high reliability, which can measure moisture in a corrosive atmosphere and which is inexpensive. Specifically, the present invention comprises a moisture-sensing element which is characterized by the fact that an electrolytic moisture-sensing mechanism consisting of (a) a pair of platinum group metal electrodes constituting an anode and a cathode, and (b) a fluororesin-type cation exchange resin membrane are integrally formed on the surface of a porous substrate which is resistant to oxidation, resistant to reduction and resistant to acids. In addition, a method for manufacturing a moisture-sensing element is provided which is resistant to oxidation, resistant to reduction and resistant to acids is coated with a solution of a fluororesin-type cation exchange resin, after an anode and a cathode are installed on the surface, and the solution is then dried and heated so that a fluororesin-type cation exchange resin membrane is formed.

Current is caused to flow between the aforementioned cathode and anode, and humidity is measured by performing a humidity-current conversion or humidity-voltage conversion according to the principle of water electrolysis.

The aforementioned electrodes and fluororesin-type cation exchange resin membrane are stably mounted on a porous substrate. Substrates of porous ceramic or porous, expanded polytetrafluoroethylene are preferred.

A covering using a porous polytetrafluoroethylene film may be installed on the outer surface of the moisture-sensing mechanism so that condensation or adhesion of water at high humidities is substantially prevented, and so that the relationship between water vapor pressure and current can be appropriately detected even in the case of an immersion-type sensor.

Examples of porous substrates resistant to oxidation, reduction and acids which can be used in the present invention include porous glass substrates, porous substrates consisting of ceramics such as $AlO_2$, $ZrO_2$, SiC, AlN, SiN and BN, and porous substrates of fluororesins such as PTFE, FEP, PFA and ETFE. A porous substrate consisting of $AlO_2$ or PTFE is especially desirable and expanded, porous PTFE as disclosed in U.S. Pat. No. 3,953,566 is most desirable in that such a material is superior in terms of corrosion resistance, has a low water absorption rate, good air permeability, adequate mechanical strength and flexibility, and is superior in terms of bonding with the fluororesin-type cation exchange resin membrane described below. The form of this substrate may be flat, tubular or columnar depending on the structure of the moisture-sensing element required.

An electrolytic moisture-sensing mechanism comprising (a) a pair of platinum group electrodes which constitute an anode and a cathode, and (b) a fluororesin-type cation exchange resin membrane, is formed on the surface of the above-mentioned porous substrate. Any of the following may be used for providing this mechanism:

(1) An anode and a cathode are formed first on the surface of the substrate, or are bonded to the substrate. Then a solution of a fluororesin-type cation exchange resin is applied, and this solution is dried and heated so that a solid coating is formed;

(2) One electrode, i.e., either the anode or the cathode, is first formed on the surface of the porous substrate, or is bonded to the substrate. Then a solution of a fluororesin-type cation exchange resin is applied, and this solution is dried and heated so that a coating is formed. Next, the other electrode, i.e., anode or cathode, which forms a pair with the first electrode formed on or bonded to the substrate as described above is formed on or bonded to the aforementioned coating. In some cases, a solution of a fluororesin-type cation exchange resin may be applied on top of this, and this solution is dried and heated so that a composite coating is formed.

(3) A solution of a fluororesin-type cation exchange resin is applied to the surface of the porous substrate, and this solution is dried and heated so that a coating is formed. Afterward, an anode and a cathode are formed on the surface of the coating. In some cases, an outer coating may also be formed by applying a solution of a fluororesin-type cation exchange resin on top of this, and then drying and heating this solution.

Of the abovementioned mechanisms (1) through (3), mechanism (1) is preferred for the following reasons: oxygen gas and hydrogen gas are generated on only one surface of the fluororesin-type cation exchange resin membrane which acts as the moisture-sensing part, i.e., on the surface located on the porous substrate side, so that the opposite surface of the membrane, which acts directly as the moisture-sensing surface, is exposed only to the gas in which moisture is to be detected. Accordingly, the humidity equilibrium is not disturbed, and the moisture-sensing area is increased.

Because the fluororesin-type cation exchange resin is acidic, and since the moisture-sensing mechanism is essentially based on water hydrolysis, so that the electrodes are exposed to nascent oxygen and hydrogen, it is desirable from the standpoint of chemical stability that the material of the electrodes be a platinum group metal such as Pt, Rh, Ir, Ru or Rd, or an alloy or oxide of such platinum group metals. Furthermore, any of the following methods may be used to form these electrodes: printing, plating, vacuum evaporation, sputtering, hot pressing following the application of a mixture with a plastic (especially PTFE), or a method in which a wire material or a foil forming a pattern is fused or simply physically bonded in place. Generally, in cases where the moisture-sensing element has a flat form, a method such as printing, plating, vacuum evaporation or sputtering is advantageous. On the other hand, in cases where the element has a columnar or tubular form, a method in which a wire material or flat strip is wound around the cylindrical element and fixed in place is desirable. In any case, adhesion between the electrodes and the coating is extremely good when the coating is formed by applying a solution of a fluororesin-type cation exchange resin and then drying and heating the applied coating after the electrodes have already been formed. However, in order to improve bonding even further in cases where a wire material or a flat strip material is used, the electrode surfaces may be mechanically roughened or subjected to a roughening treatment such as platinum black plating. In cases of weak bonding when electrodes are formed on the surface of the aforementioned fluororesin-type cation exchange resin coating, bonding can be improved by applying another solution of a fluororesin-type cation exchange resin on top of the electrodes.

Regarding the fluororesin-type cation exchange resin membrane, an ion exchange membrane using a fluorocarbon polymer as a substrate is desirable from the standpoints of oxidation resistance and heat resistance. One example of such a material is Nafion ®, a product commercially marketed by the DuPont Company. This product is a copolymer of tetrafluoroethylene and sulfonyl fluoride vinyl ether, and has sulfonic acid groups as exchange groups. In regard to solutions of this copolymer, an alcohol solution with a concentration of approximately 5% is commercially available. However, the material used in the moisture-sensing element of the present invention is not limited to this copolymer. Any material which can be obtained as a solution of a fluororesin-type cation exchange resin may be similarly used. For example, materials which have carboxyl groups as exchange groups, or materials which have groups that can be exchanged for sulfonic acid groups or carboxyl groups may also be used. In short, any material which allows stable H+ ion transmission and which can be obtained as a solution can be used. Furthermore, the output current at the time of humidity detection also varies according to the exchange group capacity. However, this does not cause any particular problems. In the present invention, it is essential that the aforementioned fluororesin-type cation exchange resin coating be formed by applying, drying and heating the abovementioned solution. This is necessary in order to form a coating which provides good bonding with the electrodes, and in order to obtain a coating which is as thin as possible. As a result of good bonding with the electrodes, a long useful life and stable performance are obtained. By forming a thin film, a sensing element with a good response time is obtained. A stable water-insoluble coating can be obtained by heating the coating after the coating is formed. The heating temperature varies according to the resin used, but is generally approximately 100° C. to 300° C. The thickness of the coating is preferably 0.5 microns or greater. The maximum thickness is generally approximately 200 microns. In particular, an element with a superior response can be obtained by making the thickness 20 microns or less. The resin coating may also be made porous by mixing a pore-forming agent with the aforementioned solution, or by mixing a poor solvent such as chlorine-type solvent, with the solution. As a result of this porosity, the relative surface area of the resin coating is increased, so that the response time is further improved. At the same time, diffusion of the gases produced is facilitated and the characteristics are stabilized. In the formation of the coating, application and drying, or application, drying and heating, may be repeated two or more times.

In the present invention, the support for the coating is limited to a porous substrate. By applying the resin solution to a porous substrate and forming a coating, the fluororesin-type cation exchange resin coating, which generally exhibits poor adhesive strength, is firmly fixed in place by an anchoring effect. As a result, the formation of a thin film is facilitated, and the state of the coating and the adhesion between the coating and the electrodes are favorably maintained over a long period of time. In order to increase the adhesion even further, it would also be possible to mix another fluororesin solution or a dispersion of PTFE or FEP with the fluororesin-type cation exchange resin solution, to apply, dry and heat said solution, to convert the ion exchange groups into metal salt groups such as $SO_2Na$ groups, and then to heat the fluororesin to a temperature above the melting point of the fluororesin, afterward again forming acid-type (e.g., $SO_3H$) ion exchange groups by means of hydrochloric acid.

In cases where the aforementioned coating is formed as described above after the electrodes have been formed first on the porous substrate, the oxygen and hydrogen gases generated at the electrodes at the time of humidity detection can be rapidly diffused through the pores in the porous substrate.

In the case of a moisture-sensing element obtained as described above, it is effective as a practical matter to form an additional covering using a porous PTFE film as a covering on the outer surface of the moisture-sensing mechanism as a protective film. Specifically, the formation of such a protective film is important (a) in order to prevent the moisture-sensing coating of the above-mentioned moisture-sensing element from deteriorating in performance due to the adhesion of oils or metal ions, (b) in order to minimize the effect of gas flow in the measurement atmosphere, (c) in order to prevent the condensation or adhesion of moisture in the case of high humidity, and (d) in order to prevent direct contact between the moisture-sensing coating and the liquid so that the relationship between water vapor pressure and current density can be detected in cases where the element is used as an immersion-type moisture detecting element. The aforementioned porous PTFE film, which effectively achieves these goals in terms of both structure and material, may be (a) integrally bonded at the time of formation of the moisture-sensing coating, using the aforementioned solution of a fluororesin-type cation exchange resin as an adhesive, or (b) simply wrapped around the element after the formation of the moisture-sensing coating or after the completion of the moisture-sensing element. If necessary, a coating of a moisture-permeable nonporous, e.g., a silicone rubber, a hydrophilic urethane or a polymer which is the same as the polymer of the moisture-sensing coating, may be formed on the outside surface of the abovementioned porous PTFE protective film.

Examples of application of the present invention follow.

EXAMPLE 1

A porous plate (10×8 mm) made of alumina, with a pore diameter of 0.2 microns, a porosity of 40% and a thickness of 0.5 mm, was prepared. Two platinum electrodes were formed by applying a platinum paste to the surface of the porous plate in a comb-like pattern by screen printing and then firing the paste.

Next, the surface of this structure was coated with a solution of a copolymer of tetrafluoroethylene and sulfonyl vinyl ether, and the solution was dried. Afterward, a coating was formed by heating the dried solution for 60 hours at 130° C. FIG. 1 shows the relationship between relative humidity RH and current density determined in a case where a voltage of 5 V was applied across the electrodes of this moisture-sensing element using a potentiostat. It was found that an extremely accurate linear correlation resulted in this case as seen in FIG. 1.

When the response of this moisture-sensing element was tested by moving the element from a humidity of 84% to a humidity of 11% at a temperature of 30° C., it was found that a more or less stable current value was established within 2 minutes.

When changes over time were investigated with this moisture-sensing element placed in an atmosphere at a temperature of 50° C. and a relative humidity of 80%, the current value showed almost no change even after 500 hours had elapsed.

EXAMPLE 2

Figure 2:
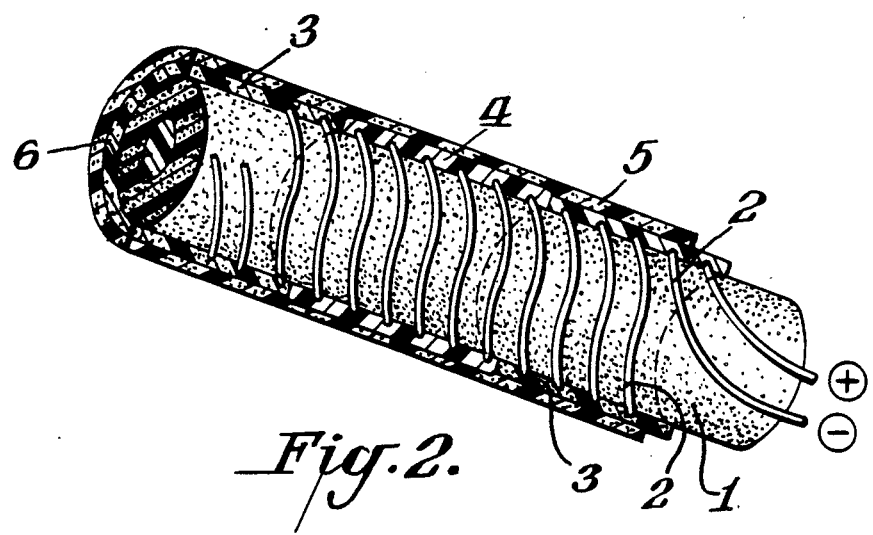
FIG. 2 is a perspective view, partly in cross-section and partly broken away, of one embodiment of the invention.

An expanded, porous PTFE tube, commercially available from W. L. Gore & Associates, Inc. as Gore-Tex ® expanded PTFE tubing, with an internal diameter of 8 mm and an external diameter of 18 mm was prepared. A piano wire with a diameter of 8 mm was inserted into the hollow space of this tube as a core material. Then, as shown in FIG. 2, two platinum wires 2 with diameters of 50 microns were wound helically at a pitch of 0.5 mm around the external surface of the PTFE tube 1 as shown in FIG. 2. The ends of these wires were fixed in place by means of an FEP heat-shrink tube 3. Next, a solution of a copolymer of tetrafluoroethylene and sulfonyl fluoride vinyl ether, constituting the aforementioned fluororesin-type ion exchange resin solution, was applied and dried. Heating for 12 hours at 150° C. was then repeated three times, so that a film 4 was formed in the moisture-sensing area. Following this, the core material was replaced by a trifluoroethylene monofilament 6 with a diameter of 8 mm, thus producing a moisture-sensing element of the type shown in FIG. 2.

Figure 3:
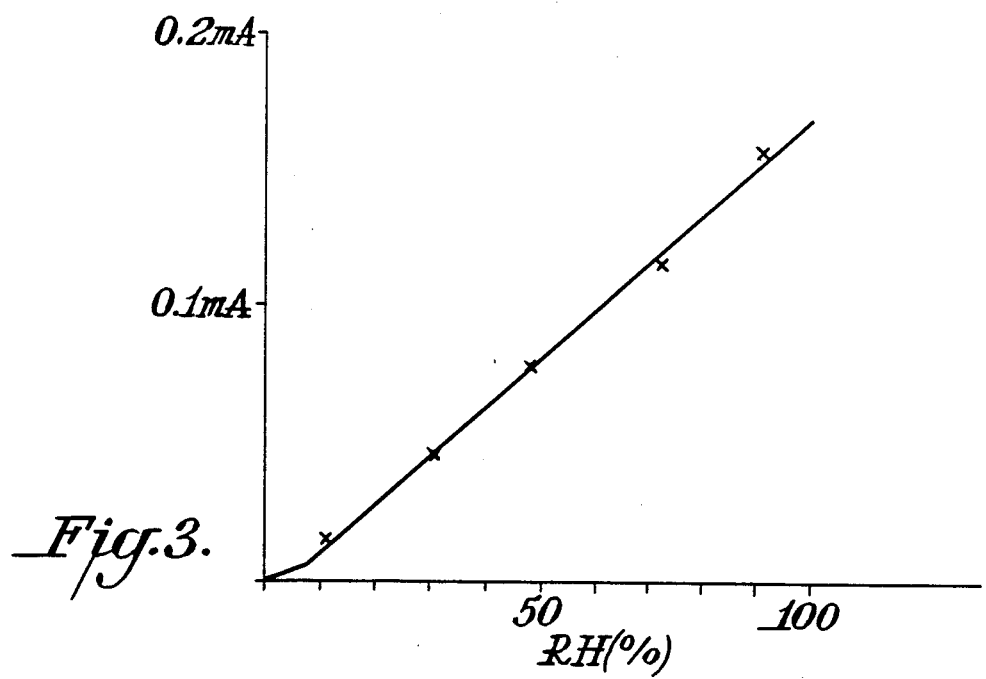
FIG. 3 is a graph indicating the relationship between current and relative humidity for the sensing element described in Example 2 below.

The relationship between relative humidity, RH, and current density in the case of the element obtained as described above was evaluated in the same manner as in Example 1. The results are shown in FIG. 3. Here, as well, it was found that there is an accurate linear correlation.

Regarding the response time of this element, a stable current value was obtained with approximately one minute. Thus, this element showed a response superior to that of the element described in Example 1 and it exhibited little change over time.

When this moisture-sensing element was covered with an expanded, porous PTFE tube 5, having internal diameter of 19 mm and external diameter of 22 mm, as a protective film, and similar tests were performed, the results obtained were similar to those described above. This element was substantially unaffected by air flow, and was thus found to be even more superior in this regard.

EXAMPLE 3

Figure 4:
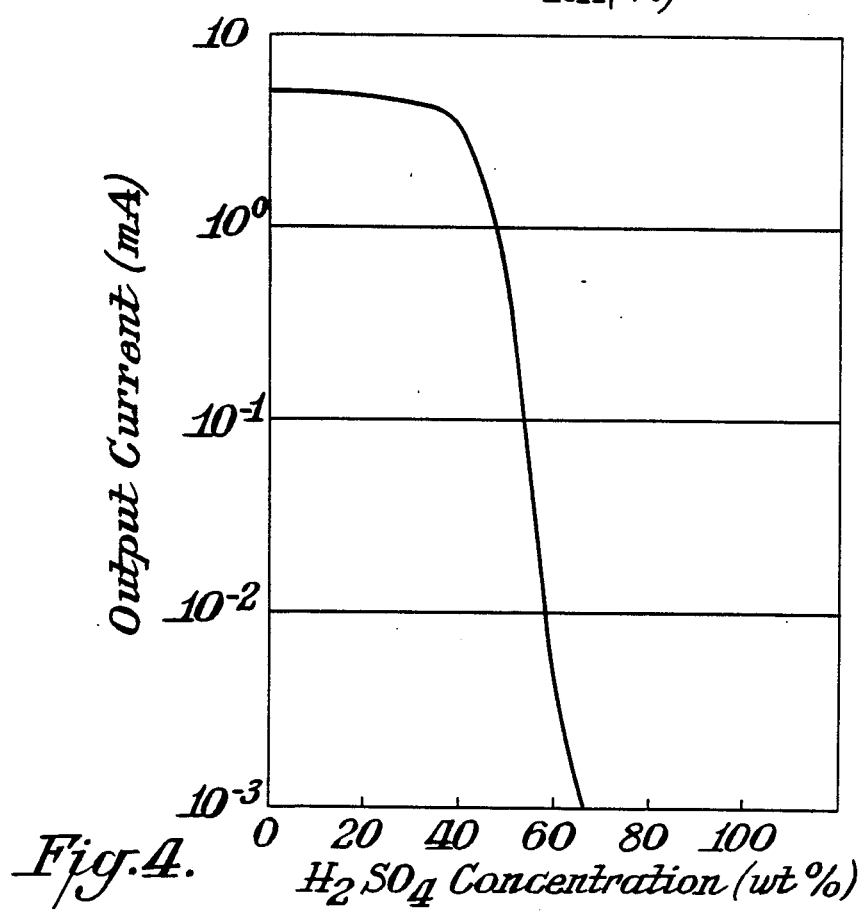
FIG. 4 is a graph which illustrates the relationship between output current and sulphuric acid concentration for a sensing element according to the invention.

The moisture-sensing element with a protective film described in Example 2 was placed in aqueous solutions of sulfuric acid with various concentrations, and the relationship between sulfuric acid concentration and current density was investigated. The results obtained are shown in FIG. 4.

This element was maintained for 500 hours with voltage applied in an aqueous solution of sulfuric acid at a temperature of 60° C., concentration of 40%, after which the relationship between sulfuric acid concentration and current was again investigated. The relationship obtained in this case was approximately the same as that shown in FIG. 4.

Tests were performed using platinum group metals other than platinum for the electrodes. In all cases, desirable results similar to those obtained in the above-mentioned examples were achieved.

As described above, the present invention makes it possible to obtain a superior-quality sensor, at relatively low cost, which has a superior response in corrosive atmospheres and in high-temperature, high-humidity atmospheres, up to 120° C., which is stable and durable, which makes it possible to measure moisture content in liquids if an appropriate hydrophobic protective film is applied and which is easy to manufacture.

While the invention has been disclosed herein in connection with certain embodiments and detailed descriptions, it will be clear to one skilled in the art that modifications or variations of such details can be made without deviating from the gist of this invention, and such modifications or variations are considered to be within the scope of the claims hereinbelow.

What is claimed is:

1. A moisture-sensing hygrometric element comprising an electrolytic moisture-sensing mechanism integrally formed on the surface of a porous substrate, said porous substrate being resistant to oxidation and reduction and resistant to acids, and wherein said moisture-sensing mechanism comprises a pair of platinum group metal electrodes constituting an anode and a cathode and having a fluororesin cation exchange resin membrane layer thereover, wherein said porous substrate is porous expanded polytetrafluoroethylene.

2. The moisture-sensing element of claim 1 wherein said cation exchange resin membrane is porous.

3. The element of claim 1 having an additional covering layer thereover of porous, expanded polytetrafluoroethylene.

* * * * *